United States Patent
Soules

[19]

[11] Patent Number: 5,898,302
[45] Date of Patent: Apr. 27, 1999

[54] RESIDUAL STRESS MEASUREMENTS IN METAL OBJECTS USING FOUR COILS

[75] Inventor: Jack Arbuthnott Soules, Shaker Heights, Ohio

[73] Assignee: Cleveland State University, Cleveland, Ohio

[21] Appl. No.: 08/978,196

[22] Filed: Nov. 25, 1997

[51] Int. Cl.[6] .......................... G01R 33/12; G01R 17/10; G01B 7/24; G01N 27/72
[52] U.S. Cl. .......................... 324/209; 324/232; 324/233; 324/234; 324/657; 324/725
[58] Field of Search .................. 324/202, 209, 324/225, 227, 232, 233, 234, 238, 610, 648, 657, 725; 73/779

[56] References Cited

U.S. PATENT DOCUMENTS

| | | | |
|---|---|---|---|
| 2,370,845 | 3/1945 | Davis | 324/209 |
| 3,132,299 | 5/1964 | Hochschild | 324/238 |
| 4,107,605 | 8/1978 | Hudgell | 324/238 X |
| 4,893,079 | 1/1990 | Kustra et al. | 324/234 X |
| 5,017,869 | 5/1991 | Oliver | 324/234 X |
| 5,329,230 | 7/1994 | Viertl | 324/238 X |
| 5,610,515 | 3/1997 | Soules | 324/209 |

*Primary Examiner*—Gerard Strecker
*Attorney, Agent, or Firm*—Jane B. Marciniszyn

[57] ABSTRACT

A device for measuring residual stress in ferromagnetic and non-ferromagnetic metal objects. The device having four electrically identical induction coils which form a four terminal alternating current bridge circuit. There is a fine wire shield formed of fingers for shielding the coils from stray capacitance. The bridge having four coil terminals. Two diagonally opposite coil terminals are connected to a variable frequency constant voltage generator. The other two diagonally opposite coil terminals are connected to a low noise broad band preamplifier. The preamplifier amplifies any unbalance in the bridge. There is a double pole double throw switch connected to two coil terminals which are diagonally opposite each other. Connected to the preamplifier is an amplifier. The amplifier is connected to a phase detector which is connected to a computer. The phase detector detects in phase and quadrature component signals. The computer has software for determining changes in differential resistivity as a function of frequency, and for converting resistivity differences into residual stress using an algorithm.

11 Claims, 2 Drawing Sheets

5,898,302

RESIDUAL STRESS MEASUREMENTS IN METAL OBJECTS USING FOUR COILS

TECHNICAL FIELD

The present invention relates to the generation of eddy currents and more particularly to a sensitive test method and equipment for determining the residual stress in both ferromagnetic and non-ferromagnetic metal objects using eddy currents.

BACKGROUND OF THE INVENTION

In industrial situations some metals, e.g., titanium, aluminum, steel alloys and stainless steel, are shot-peened in order to increase the residual stress in the metal object. As a non-destructive test procedure, eddy current measurements are employed to determine whether the entire surface of the metal object was shot peened and whether the residual stress has the correct distribution with respect to the depth in the metal object. In other instances eddy currents are used to determine surface and sub-surface cracks or flaws in metal objects. Such defects produce relatively large changes in the induced currents and common eddy current equipment easily detects these changes. The SmartEddy™ system, manufactured by SES Corporation, Menlo Park, Calif., uses a two resistor, two coil bridge to detect amplitude and phase shifts produced by treated metal objects compared to a test standard. U.S. Pat. No. 5,610,515 modified the SmartEddy™ system to improve its sensitivity in determining residual stress in treated non-ferromagnetic metal objects by reducing the sensitivity of the apparatus to vibration and temperature changes.

Current induced into a metal object by an external coil is called eddy current. The use of eddy current technique to characterize the properties of metal objects is based on the relationship between a conductive metal object structure and electromagnetic properties. More specifically, eddy current testing relies on electromagnetic interaction between the coil driven by an alternating electrical current and the metal object under test. In order to measure applied or residual stresses with a conventional eddy current approach, the application of stress must change the electrical conductivity such that a detectable change in the test coil impedance will occur.

Presently, current commercial eddy current equipment is not sensitive enough to detect extremely small changes in conductivity in a treated metal object. Nor is present commercial eddy current equipment sensitive enough to detect changes in conductivity at the near-surface of a treated metal object, i.e., within 0.020 inch.

It is an object of the present invention to provide a method and equipment to detect very small changes in conductivity between a treated metal object and an untreated metal object sample used as a reference.

It is another object of the present invention to be operated at a wide range of frequencies thereby checking the sample at various depths.

It is another object of the present invention to be operated at high frequency in order to measure conductivity at the near-surface of a treated metal object.

It is a further object of the present invention to determine the residual stress of a metal object that has been subject to machining, shot-peening or other chemical and mechanical treatments.

It is a still further object of the present invention to avoid ambiguous results due to mechanical vibration and lift-off as the test coil is brought close to the sample.

These and further important objects of the present invention will become more apparent upon considering the following detailed description of the present invention.

SUMMARY OF THE INVENTION

The method of this invention for determining residual stress in both ferromagnetic and non-ferromagnetic metal objects comprises the steps of: contacting simultaneously the surfaces of a treated and untreated metal object with four spaced apart identical induction coils, two coils for each metal object, the four coils form a four terminal balanced alternating current bridge circuit having two diagonals; connecting a double pole double throw switch between two diagonally opposite coil terminals for interchanging two of the coils of the bridge by exchanging a coil on the treated metal object with a coil on an untreated metal object to produce a maximum asymmetry in the bridge configuration; connecting two diagonally opposite corners of the bridge to a variable frequency constant voltage generator; connecting the other diagonally opposite corners of the bridge to a low noise broad band preamplifier, wherein the preamplifier amplifies any unbalance in the bridge; connecting the broad band preamplifier to an amplifier; connecting the amplifier to a phase detector; energizing the bridge in the frequency range of 10 kHz to 200 MHz causing current flow in the coils; detecting an in phase component signal and a quadrature component signal when the bridge is in nearly symmetric configuration; interchanging two of the coils of the bridge using the double pole double throw switch; energizing the bridge in the frequency range of from 10 kHz to 200 MHz causing current flow in said induction coils; detecting in phase component and quadrature component of the unbalanced signals when the bridge is in an unsymmetric configuration; subtracting the signals in the nearly symmetric configuration from the signals in the asymmetric configuration to determine a difference as a function of frequency, determining changes in differential resistivity as a function of frequency wherein low frequency penetrates said treated and untreated metal objects more deeply than a higher frequency; and converting a resistivity difference between the treated and untreated metal objects into residual stress created in the treated metal object using an algorithm.

The method of this invention may be carried out using a device for measuring residual stress in a treated metal object which comprises four spaced apart coils of identical inductance which form a four terminal alternating current bridge circuit and suitable for operation in a frequency range of from 10 kHz to 200 MHz, a double pole double throw switch between two diagonally opposite coil terminals, wherein the switch interchanges two of the coils of the bridge, and a variable frequency constant voltage generator. The variable frequency constant voltage generator is connected to diagonally opposite coil terminals. The device further includes a low noise broad band preamplifier, wherein the preamplifier amplifies an unbalance in the bridge. The low noise broad band preamplifier is connected to the other diagonally opposite coil terminals. The device further includes a means for detecting in phase and quadrature components, a means for determining changes in differential resistivity as a function of frequency, and a means for converting resistivity differences into residual stress using an algorithm.

Another embodiment of the device for measuring residual stress in a treated metal object comprises four flat identical induction coils positioned on a substrate, wherein the four coils are spaced apart so as to prevent any mutual inductance effects and wherein the four coils form a four terminal balanced alternating current bridge circuit having two diagonals and suitable for operation in a frequency range of from about 10 kHz to 200 MHz. The four coils are shielded from stray capacitance by a fine wire shield formed of fingers. The device having a double pole double throw switch between two diagonally opposite coil terminals, and a variable frequency constant voltage generator which is connected to diagonally opposite coil terminals. There is a low noise broad band preamplifier, wherein the preamplifier amplifies an unbalance in the bridge and the preamplifier is connected to two other diagonally opposite coil terminals. The device also including an amplifier and a phase detector. The device further including a means for detecting in phase and quadrature components, a means for determining changes in differential resistivity as a function of frequency, and a means for converting differences into residual stress using an algorithm.

The various features and advantages of the invention will become more apparent from the detailed description of a preferred embodiment of the invention when considered along with the accompanying drawings.

BEST MODE FOR CARRYING OUT THE INVENTION

Figure 1:
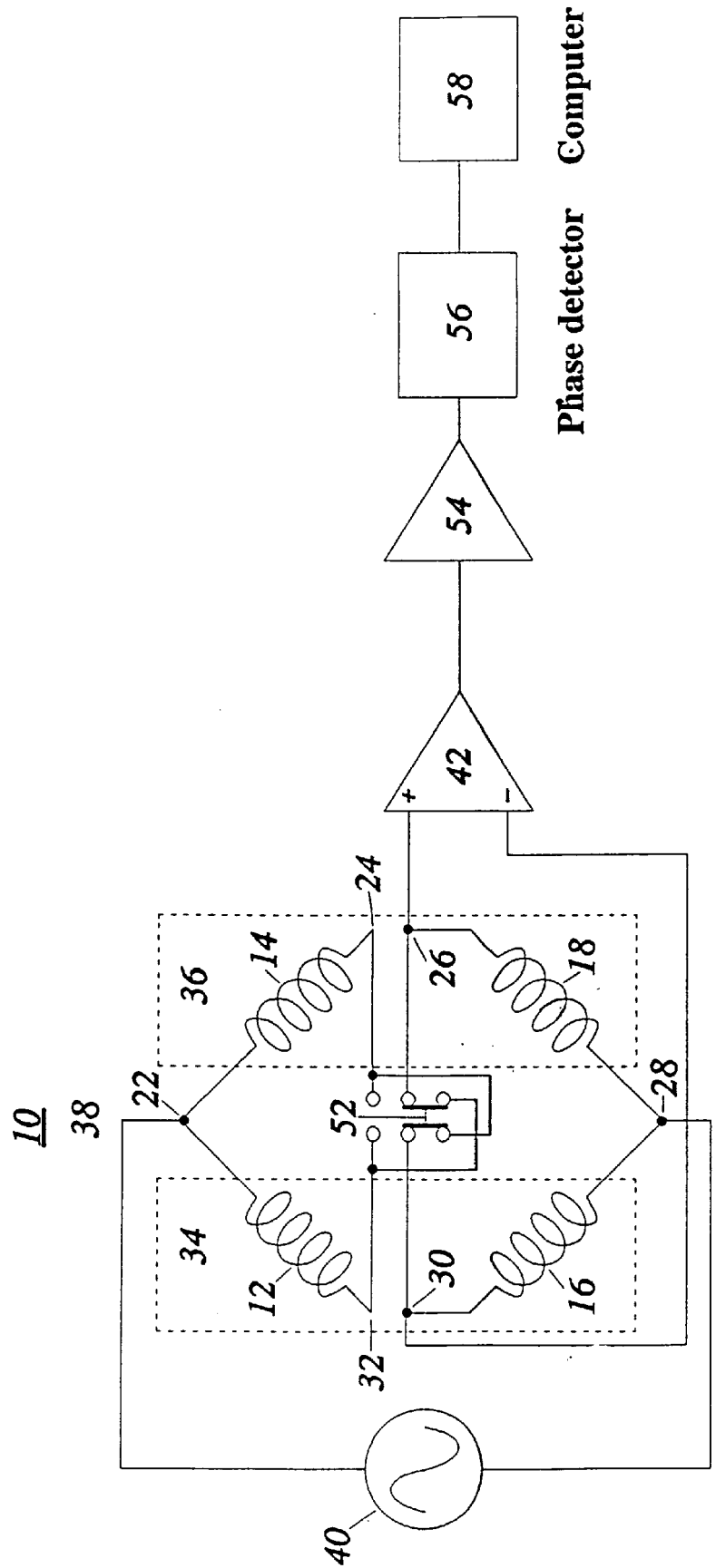
FIG. 1 is a circuit diagram embodying the present invention.
Figure 2:
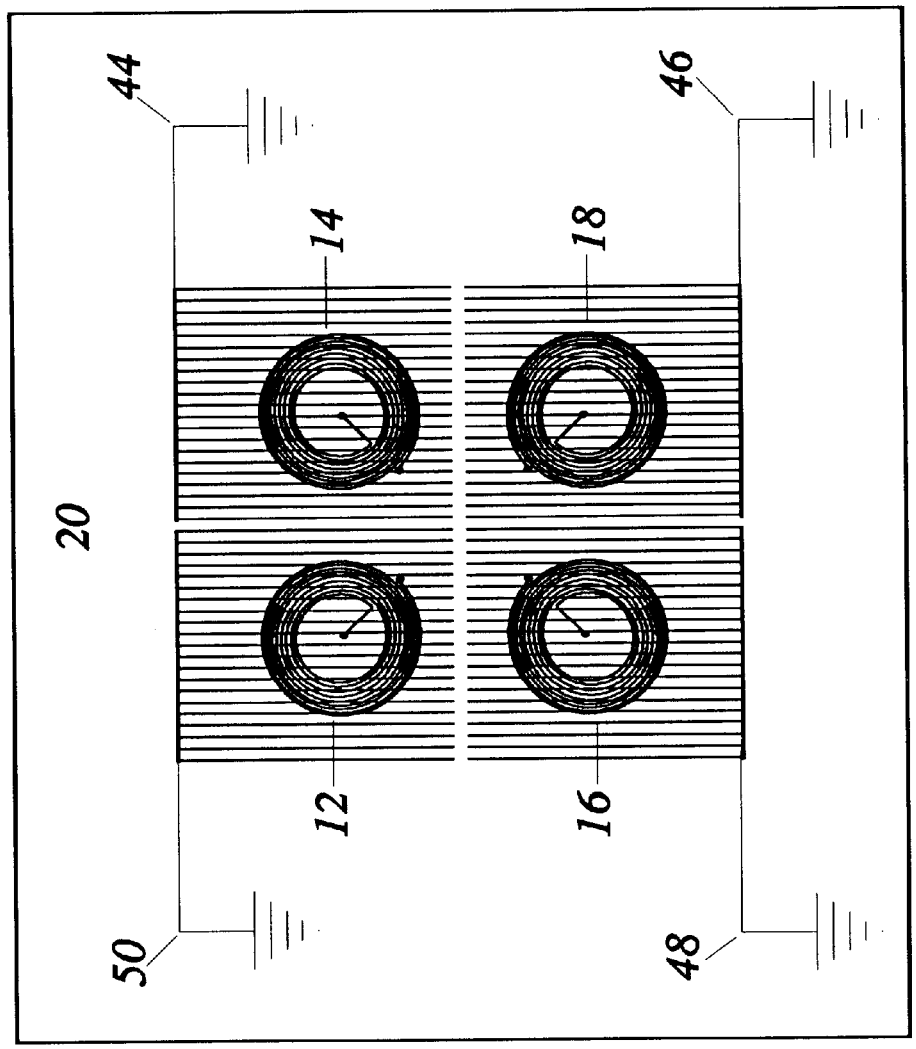
FIG. 2 is a flat surface having four induction coils.

Referring to the drawings in greater detail, and first to FIG. 1, the invention is incorporated in a device for determining residual stress in both ferromagnetic and non-ferromagnetic metal objects, generally designated 10, which includes four spaced apart flat identical induction coils, 12, 14, 16, 18. One embodiment has the coils loose and the other embodiment has the coils positioned on a substrate 20 (FIG. 2). The substrate can be any plastic, ceramic or other suitable material that is flat with a low dielectric loss, preferably Teflon®. The four coils are spaced far enough apart to prevent any mutual inductance effects or interacting magnetic fields. The coils have an inductance of about 8 microhenries to about 1 microhenry depending upon the chosen frequency range. The coils can be electrically similar and geometrically dissimilar in order to permit testing of the metal object if it has different contours. The four coils form a four terminal balanced alternating current bridge circuit, 22, 24–26, 28, 30–32. A treated metal object 34 is placed on two coils, e.g., 12 and 16, and an untreated metal object 36 is placed on the other two coils, e.g., 14 and 18. The metal objects can be aluminum, steel, stainless steel, nickel-cobalt-steel and titanium. The device will be sensitive to very small changes in conductivity. The treated metal object can be stressed to a minimum depth in order to strengthen the metal object, e.g., to 0.020 inches. The metal object can be stressed by machining, shot preening or other mechanical means. Eddy currents can also detect changes in the electrical conductivity of the surface due to carburizing, nitriding, and heat treatment. In a ferromagnetic metal object the alternating current is held to a few milliamperes to produce a field of about 1×10–4 Tesla or less. The bridge 38 has two pairs of diagonal coil terminals. Two coil terminals e.g., 22 and 28 are connected to a variable frequency constant voltage generator 40. The generator 40 generates a frequency range of 10 kHz to 200 MHz. The lower frequencies penetrate a depth greater than higher frequencies. It is desirable to sample the surface of the metal object at various depths. The two coil terminals are diagonally opposite each other. The other two diagonal coil terminals, 26–30 or 24–32 connect to those terminals either in this order or the reverse order and are connected to a low noise broad band preamplifier 42. Each coil is shielded from stray capacitance by a fine wire shield formed of fingers 44, 46, 48, 50. Between two pairs of diagonally opposite coil terminals is a double pole double throw reversing switch 52. The switch connects terminals 26–30 to terminals 24–32 or to terminals 32–24 depending on the position of the switch. The preamplifier 42 is connected to an amplifier 54. The amplifier 54 is connected to a phase detector 56. The phase detector 56 is connected to a computer 58. The phase detector 56 detects in phase and quadrature component signals. The computer 58 has several different software programs. Using the in phase and quadrature component signals, one program determines changes in differential resistivity as a function of frequency. The second software program converts resistivity differences into residual stress using an algorithm.

To determine the residual stress of a treated ferromagnetic or non-ferromagnetic metal object, a user will simultaneously contact the surface of the-treated metal object 34 and the untreated metal object 36 with 4 induction coils, 12, 14, 16 and 18. Two coils are on the surface of each metal object, e.g., 12 and 16, 14 and 18. The coils are arranged geometrically to have non-interacting magnetic fields. The coils will form a four terminal 22, 24–26, 28 and 30–32 balanced alternating bridge circuit, 38. There will be two diagonally opposite coil terminals e.g., 22 and 28, 24–32 and 26–30 as shown in FIG. 1. A double pole double throw reversing switch 52 is connected to two diagonally opposite coil terminals, e.g., 24–26 and 30–32. Two diagonally opposite coil terminals, e.g., 22 and 28, are connected to a variable frequency constant voltage generator, 40. Placed over each coil is a fine wire shield formed of fingers, 44, 46, 48 and 50. Two of the diagonally opposite coil terminals, e.g., 26 and 30 or equivalently 24 and 32, are connected to a low noise broad band preamplifier 42. The preamplifier, 42, amplifies any unbalance in the bridge. The preamplifier, 42, is connected to an amplifier, 54, which is connected to a phase detector, 56. The phase detector, 56, is connected to a computer, 58, having several software programs. After all these connections are made, the bridge is energized in the frequency range of 10 kHz to 200 MHz causing current to flow in the coils, i.e., 22 to 14 to 24 to 26 to 18 to 28 and 22 to 12 to 32 to 30 to 16 to 28. Lower frequencies penetrate the metal object more deeply than higher frequencies. The current is held to a few milliamperes to produce a field of 10–4 Tesla or less for any ferromagnetic metal objects. The phase detector 56 detects an in phase component signal and a quadrature component signal when the bridge is in a nearly symmetrical configuration. If all the circuit elements and the samples were ideal the bridge would be perfectly balanced. In practice a small error signal is detected due to slight differences in the test coil and/or sight point to point variations in the samples. Next the coils are interchanged using the double pole double throw reversing switch 52. The interchanging of the coils by exchanging a coil on a treated metal object with a coil on the untreated metal object produces a maximum asymmetry in the bridge configuration. After the interchange of the coils, the bridge is energized in a frequency range of 10 kHz to 200 MHz causing current to flow in the coils, i.e., 22 to 14 to 24 to 30 to 16 to 28 and 22 to 12 to 32 to 26 to 18 to 28 as shown is FIG. 1. The next step is detecting the in phase component and quadrature component of the unbalanced signals when the bridge is in the asymmetrical configuration. The values secured for the in phase and quadrature components from energizing the coils while in the nearly symmetric configuration are subtracted from the value secured while the coils are in the asymmetric configuration. These values are a function of specific frequencies. Software is used to determine the changes in differential resistivity, and convert the resistivity changes between the treated and untreated metal objects into residual stress in the treated metal object using an algorithm. This method can be used on the entire surface of the metal object, point by point to determine whether the metal object has been properly treated and whether the residual stress has the correct distribution with respect to the depth in the metal object over the entire surface.

The present invention has been described with a degree of particularity. It is the intent, however, that the invention include all modification and alterations from the disclosed embodiments falling within the spirit or scope of the appended claims.

What is claimed is:

1. A test method to determine residual stress in ferromagnetic and non-ferromagnetic metal objects which comprises:
    a. contacting simultaneously a surface of a treated and an untreated metal object with four spaced apart identical induction coils, two coils for each metal object, wherein said four coils form a four terminal balanced alternating current bridge circuit having two diagonals;
    b. connecting a double pole double throw switch between two diagonally opposite coil terminals for interchanging two of said coils of said bridge by exchanging a coil on said treated metal object with a coil on said untreated metal object to produce a maximum asymmetry in said bridge configuration;
    c. connecting two diagonally opposite corners of said bridge to a variable frequency constant voltage generator;
    d. connecting said other diagonally opposite corners of said bridge to a low noise broad band preamplifier, wherein said preamplifier amplifies any unbalance in said bridge;
    e. connecting a broad band amplifier to said preamplifier;
    f. connecting said amplifier to a phase detector;
    g. energizing said bridge in said frequency range of from 10 kHz to 200 MHz causing current flow in said induction coils;
    h. detecting an in phase component signal and a quadrature component signal when said bridge is in a nearly symmetric configuration;
    i. interchanging two of said coils of said bridge using said double pole double throw switch;
    j. energizing said bridge in said frequency range of from 10 kHz to 200 MHz causing current flow in said induction coil;
    k. detecting in phase component and quadrature component of said unbalanced signals when said bridge is in an asymmetric configuration;
    l. subtracting said signals in step h from said signals in step k for said in phase component and said quadrature components to determine a difference as a function of frequency;
    m. determining changes in differential resistivity as a function of frequency wherein said low frequency penetrates a sample more deeply than a higher frequency; and
    n. converting resistivity differences between said treated and untreated metal objects into residual stress created in said treated metal object using an algorithm.

2. The method according to claim 1 wherein said coils have an inductance of from about 8 microhenries to about 1 microhenry.

3. The method according to claim 1 wherein coils are arranged geometrically in said bridge to have non-interacting magnetic fields.

4. The method according to claim 1 wherein said ferromagnetic sample AC current is held to a few milliampere to produce a field of about 1×10−4 Tesla or less.

5. The method of claim 1 wherein two coils are electrically similar and geometrically dissimilar in order to permit testing of said metal objects having different contours.

6. The method of claim 1 wherein four coils are electrically similar and geometrically dissimilar in order to permit testing of said metal object having different contours.

7. A device for measuring the residual stress in a treated metal object and an untreated metal object comprising:
    a. four spaced apart identical induction coils which form a four terminal balanced alternating current bridge circuit having two diagonals and suitable for operation in a frequency range of from 10 kHz to 200 MHz;
    b. a double pole double throw reversing switch between two diagonally opposite coil terminals constituting a first of said two diagonals, wherein said switch interchanges two of said coils of said bridge;
    c. a variable frequency constant voltage generator connected to diagonally opposite coil terminals constituting a second of said two diagonals;
    d. a low noise broad band preamplifier, wherein said preamplifier amplifies an unbalance voltage in said bridge, wherein said preamplifier is connected to said pair of diagonally opposite coil terminals constituting said first diagonal;
    e. an amplifier connected to said preamplifier;
    f. a means coupled to said amplifier for detecting the in phase and quadrature components of a signal from said amplifier wherein in phase is with respect to said voltage of said voltage generator;
    g. a means for interpreting changes in said in phase and quadrature components as a function of frequency to infer changes in material resistivity;
    h. a means for converting resistivity differences obtained from said inferred changes in material resistivity into residual stress differences.

8. The device of claim 7 wherein said coils have an inductance of from about 8 microhenries to about 1 microhenry.

9. The device of claim 7 wherein said coils are arranged geometrically in said bridge to have non-interacting magnetic fields.

10. The device of claim 7 wherein the alternating current is held to a few milliampere to produce a field of about 1×10−4 Tesla or less when said metal objects are ferromagnetic.

11. A device for measuring the residual stress in treated metal objects and untreated metal objects comprising:
    a. four flat identical induction coils positioned on a substrate, wherein said coils are spaced apart so as to prevent any mutual inductance effects and wherein said four coils form a four terminal balanced alternating current bridge circuit having two diagonals and suitable for operation in a frequency range of from about 10 kHz to 200 MHz;
    b. a fine wire shield formed of fingers, wherein said fingers shield said four coils from stray capacitance;

c. a double pole double throw reversing switch between two diagonally opposite coil terminals constituting a first of said two diagonals;

d. a variable frequency constant voltage generator connected to diagonally opposite coil terminals constituting a second of said two diagonals;

e. a low noise broad band preamplifier, wherein said preamplifier amplifies an unbalance voltage in said bridge and said preamplifier is connected to said pair of diagonally opposite coil terminals;

f. an amplifier connected to said preamplifier;

g. a means coupled to said amplifier for detecting the in phase and quadrature components of a signal from said amplified wherein in phase is with respect to said voltage of said voltage generator;

h. a means for interpreting changes in said in phase and quadrature components as a function of frequency to infer changes in material resistivity;

i. a means for converting resistivity differences obtained from the inferred changes in material resistivity into residual stress differences.

* * * * *